United States Patent
Dave et al.

(10) Patent No.: US 10,544,066 B2
(45) Date of Patent: Jan. 28, 2020

(54) MICROENCAPSULATED NITRIFICATION INHIBITOR COMPOSITIONS

(71) Applicant: DOW AGROSCIENCES LLC, Indianapolis, IN (US)

(72) Inventors: Hiteshkumar Dave, Collegeville, PA (US); Lei Liu, Jr., Indianapolis, IN (US); Raymond E. Boucher, Indianapolis, IN (US); Greg Powels, Indianapolis, IN (US); Alex Williams, Indianapolis, IN (US); Miriam Tudyk, Lafayette, IN (US); Martin C. Logan, Indianapolis, IN (US); Mini Jan, Freeport, TX (US)

(73) Assignee: Dow AgroSciences LLC, Indianapolis, IN (US)

( * ) Notice: Subject to any disclaimer, the term of this patent is extended or adjusted under 35 U.S.C. 154(b) by 91 days.

(21) Appl. No.: 15/540,827

(22) PCT Filed: Dec. 23, 2015

(86) PCT No.: PCT/US2015/000217
§ 371 (c)(1),
(2) Date: Jun. 29, 2017

(87) PCT Pub. No.: WO2016/108928
PCT Pub. Date: Jul. 7, 2016

(65) Prior Publication Data
US 2017/0369386 A1    Dec. 28, 2017

Related U.S. Application Data
(60) Provisional application No. 62/098,974, filed on Dec. 31, 2014.

(51) Int. Cl.
| | | |
|---|---|---|
| *A01N 25/04* | (2006.01) | |
| *C05G 3/08* | (2006.01) | |
| *C05G 3/02* | (2006.01) | |
| *C05G 3/00* | (2006.01) | |

(52) U.S. Cl.
CPC .............. *C05G 3/08* (2013.01); *A01N 25/04* (2013.01); *C05G 3/0017* (2013.01); *C05G 3/0029* (2013.01); *C05G 3/02* (2013.01)

(58) Field of Classification Search
None
See application file for complete search history.

(56) References Cited

U.S. PATENT DOCUMENTS

| 4,808,206 A | 2/1989 | Smith | |
| 2008/0176745 A1* | 7/2008 | Wilson ................... | C05G 3/08 504/101 |
| 2009/0227458 A1* | 9/2009 | Boucher, Jr. ............ | C05G 3/08 504/244 |
| 2009/0269382 A1* | 10/2009 | Mulqueen .............. | A01N 25/28 424/408 |
| 2011/0045975 A1 | 2/2011 | Ehr et al. | |
| 2011/0301036 A1* | 12/2011 | Tank ...................... | A01N 25/28 504/347 |
| 2015/0315091 A1 | 11/2015 | Dave et al. | |

OTHER PUBLICATIONS

International Searching Authority, International Preliminary Report on Patentability for PCT/US2015/000217, dated Jul. 13, 2017, 7 pages.

* cited by examiner

*Primary Examiner* — Wayne A Langel

(57) ABSTRACT

The present disclosure relates to an improved nitrification inhibitor composition and its use in agricultural applications.

28 Claims, No Drawings

MICROENCAPSULATED NITRIFICATION INHIBITOR COMPOSITIONS

CROSS REFERENCE TO RELATED APPLICATION

This application is a U.S. National Phase Patent Application based on International Application No. PCT/US2015/000217, which claims priority to U.S. Provisional Patent Application Ser. No. 62/098,974, filed Dec. 31, 2014, the disclosures of which are hereby expressly incorporated by reference herein in their entirety.

FIELD OF THE INVENTION

The present invention relates to improved nitrification inhibitor compositions, methods of making the same, and their use in agricultural applications.

BACKGROUND AND SUMMARY

Nitrogen fertilizer added to the soil is readily transformed through a number of undesirable biological and chemical processes, including nitrification, leaching, and evaporation. Many transformation processes reduce the level of nitrogen available for uptake by the targeted plant. One such process is nitrification, a process by which certain widely occurring soil bacteria metabolize the ammonium form of nitrogen in the soil, transforming the nitrogen into nitrite and nitrate forms, which are more susceptible to nitrogen loss through leaching or volatilization via denitrification.

The decrease in available nitrogen due to nitrification necessitates the addition of more nitrogen rich fertilizer to compensate for the loss of agriculturally active nitrogen available to the plants. These concerns intensify the demand for improved management of nitrogen, in order to reduce costs associated with the use of additional nitrogen fertilizer.

Methods for reducing nitrification include treating soil with agriculturally active compounds that inhibit or at least reduce the metabolic activity of at least some microbes in the soil that contribute to nitrification. These compounds include (Trichloromethyl)pyridines, such as nitrapyrin, which have been used as nitrification inhibitors in combination with fertilizers as described in U.S. Pat. No. 3,135,594, the disclosure of which is incorporated herein by reference in its entirety. These compounds help to maintain agriculturally-applied ammonium nitrogen in the ammonium form (stabilized nitrogen), thereby enhancing plant growth and crop yield. These compounds have been used efficaciously with a number of plant crops including corn, sorghum, and wheat.

Compounds such as nitrapyrin are unstable in soil in part because they are very volatile. For example, nitrapyrin has a relatively high vapor pressure ($2.8 \times 10^{-3}$ mm Hg at 23° Celsius), and because of this it has a tendency to volatilize and must be applied immediately or somehow protected from rapid loss after the fertilizer is treated with nitrapyrin. One approach is to add nitrapyrin to a volatile fertilizer, namely anhydrous ammonia, which itself must be added to the soil in a manner that reduces the amount of the volatile active lost to the atmosphere. This method is problematic in that it requires the use of anhydrous ammonia, which is corrosive and must be injected into the soil. This method of applying nitrapyrin, while stabilizing nitrapyrin below the soil surface, is not preferred. This method is unsuitable for many other fertilizer types and their standard application practices such as dry fertilizer granules, which most often are broadcasted onto the soil surface.

Still other approaches to stabilize nitrapyrin and reduce its loss to the atmosphere include applying it to the surface of the soil and then mechanically incorporating it into the soil, or watering it into the soil generally within 8 hours after its application to reduce its loss to the atmosphere. Still another approach is to encapsulate nitrapyrin for rapid or dump release. Such encapsulated forms of nitrapyrin have been formulated with lignin sulfonates as disclosed in U.S. Pat. No. 4,746,513, the disclosure of which is incorporated herein by reference in its entirety. While these formulations are less volatile than simple nitrapyrin, these formulations are better suited for use with liquid urea ammonium nitrate ("UAN") or liquid manure fertilizers than with dry fertilizers. Although the release of nitrapyrin is delayed by the encapsulation, the capsules release all of the nitrapyrin upon contact with moisture, exhibiting the same stability and volatility disadvantages of the prior application methods.

Another approach to stabilizing nitrapyrin includes polycondensation encapsulation. Additional information regarding this approach can be found in U.S. Pat. No. 5,925,464, the disclosure of which is incorporated herein by reference in its entirety. Some of these formulations enhance handling safety and storage stability of the nitrapyrin using polyurethane rather than polyurea to form at least a portion of the capsule shell.

In some instances, polyurea microencapsulation has been used to produce enhanced nitrification inhibitor compositions for delayed, steady release of nitrification inhibitors for application with fertilizers. Such encapsulated forms of nitrapyrin are disclosed in U.S. Pat. Nos. 8,377,849 and 8,741,805, the disclosures of which are incorporated herein by reference in their entirety.

There remains a need to deliver nitrification inhibitors such as, for example, (trichloromethyl)pyridines having greater long term stability in the field environment, while maintaining the level of efficacy of unencapsulated inhibitors.

While microcapsule aqueous suspensions (a.k.a. capsule suspensions or "CS") of microencapsulated nitrapyrin referred to above are more stable than un-encapsulated nitrapyrin in an aqueous solution under certain conditions, it has been observed that crystals of nitrapyrin can form in the aqueous phase of a microcapsule suspension of nitrapyrin. Formation of crystalline nitrapyrin in an aqueous microcapsule suspension of nitrapyrin appears to be favored over a narrow temperature range of about −5° C. to about 15° C., more particularly about 0° C. to about 10° C. (degrees centigrade). The weight percentage of crystalline nitrapyrin in the bulk aqueous phase of the microcapsule suspension accumulates over time. Depending upon how the microcapsule suspensions are handled, the presence of measurable levels of crystalline nitrapyrin in the aqueous phase can be of little-to-no consequence or problematic. The presence of even about 0.1 wt. percent crystalline nitrapyrin or above in the aqueous phase of the microcapsule suspension can be especially problematic if the suspension is applied by spraying the suspension through a fine point nozzle with a sprayer containing inline screens.

Additionally, certain commercial embodiments of polyurea microencapsulated nitrification inhibitors, such as, for example, Instinct® or Entrench® (commercial embodiments sold by Dow AgroSciences LLC), are limited by the amount of active ingredient (nitrification inhibitor) that can be microencapsulated and suspended in the aqueous phase without the active ingredient crystallizing into the aqueous phase. For example, in some embodiments, Instinct® and Entrench® comprise about 17% to about 18% by weight active ingredient (nitrapyrin). Crystallization of the active ingredient into the aqueous phase has limited increased levels of active in these aqueous capsule suspensions. Some commercial nitrapyrin capsule suspension formulations have active loadings of 200 g/L, the upper limit of the loading being bound by the solubility of the nitrapyrin in the solvent.

In some of the inventive embodiments of the present disclosure, no solvent is required to dissolve the nitrapyrin (and/or other active ingredient) in the lipophilic phase. In some embodiments, stable aqueous capsule suspension formulations up to 300 g/L nitrapyrin loading are disclosed, without crystallization issues.

Some aspects of the present disclosure include compositions that prevent and/or reduce crystal formation issues observed in presently commercially available formulations of nitrapyrin, including capsule suspensions. Crystal formation in nitrification inhibiting compositions can cause problems including filter blockage during field spray applications. In some instances, crystals that form in the liquid phase of a capsule suspension are high purity crystals, comprising substantially pure organic nitrification inhibitor, such as, for example, nitrapyrin. In some instances, high purity nitrapyrin (99 wt %) crystals form in presently available commercial formulations. Crystal formation, in some instances, is dependent upon the temperature of the formulation in storage, shipping, and/or transport of the formulations.

In some embodiments of the microcapsule suspension formulations of the present disclosure, stable, high-load, agricultural liquid formulations comprising aqueous microcapsule suspensions containing low melting active ingredients are presented. In some embodiments, the microcapsule suspension formulations are prepared without use of an organic solvent to dissolve the low melting point active, such as for example a nitrification inhibitor such as nitrapyrin, and may optionally use small amounts of a polymeric ultra-hydrophobe to prepare the microcapsules. In some embodiments, the microcapsule suspension formulation may include a hydrophobic crystal inhibitor additive to prevent or inhibit crystal formation or growth of the nitrapyrin. In some embodiments, the formulations provide superior physical, chemical, and/or crystallization stability upon storage, and acceptable volatility and nitrification inhibition attributes in applications to the soil.

In some embodiments of the microcapsule suspension formulations disclosed herein, post addition (i.e. after microcapsule formation) of a hydrophobic crystal inhibitor additive to the aqueous phase reduces the rate of crystal formation and/or growth in the aqueous phase at certain temperature storage conditions. In one embodiment, post addition of one or more hydrophobic crystal inhibitor additives provides superior crystal growth reduction in cold temperature storage conditions. In one exemplary embodiment, post-addition of a hydrophobic crystal inhibitor additive that is an aromatic solvent, which includes at least one oil, is present in the aqueous phase of the formulation after the formation of the microcapsules. The term "oil" will herein describe organic solvents that are generally immiscible with water.

In some embodiments, microcapsule suspension formulations already containing crystals of nitrapyrin and without a hydrophobic crystal inhibitor additive in the aqueous phase can be treated with one or more hydrophobic crystal inhibitor additives by addition to the aqueous phase, and the resulting mixture can be stirred at ambient temperature for a length of time, possibly 30 minutes to 5 hours based on the total volume of the microcapsule suspension, until the crystals of nitrapyrin, and/or other crystallized organic inhibitor of nitrapyrin, have disappeared.

The present disclosure therefore provides compositions and methods to prevent and/or reduce crystals and crystal formation in stable, high-load agricultural active compositions containing organic nitrification inhibitors, such as nitrapyrin. In some embodiments, addition of hydrophobic crystal inhibitor additives prevent and/or reduce crystals and crystal formation in capsule suspensions of microencapsulated nitrapyrin. In some embodiments, hydrophobic crystal inhibitor additives provide superior physical stability at about 10° C. stability testing.

In certain embodiments, hydrophobic crystal inhibitor additives of the present disclosure could be applied to any agricultural active composition comprising one or more solvents, one or more agricultural active ingredients, and/or one or more nitrification inhibitors, optionally nitrapyrin.

In certain embodiments, in the absence of the addition of one or more hydrophobic crystal inhibitor additives to the aqueous phase, the microcapsule suspension formulations of the present application may form nitrapyrin crystals in the aqueous phase at cold storage temperatures of about 10° C. These nitrapyrin crystals may be about 99% pure. Over time, such crystals may compose up to 0.5 weight percent of the overall microcapsule suspension formulation. Crystals may also form at other temperatures, such as 0° C.-5° C., and 15° C. Solvent-based, hydrophobic crystal inhibitor additives such as aromatic solvents and ester compounds can increase the physical stability of the microcapsule suspension formulations, particularly at mild cold storage temperatures of about 10° C., preventing or at least reducing crystal formation in the aqueous phase of the microcapsule suspension.

Illustratively, post-added aromatic solvents used as hydrophobic crystal inhibitor additives include: Aromatic 100 Fluid, also known as solvent naphtha or light aromatic; Aromatic 150 Fluid, also known as solvent naphtha, heavy aromatic, high flash aromatic naphtha type II, heavy aromatic solvent naphtha, hydrocarbons, C10 aromatics, >1% naphthalene, A150, S150 (Solvesso 150); and Aromatic 200 Fluid, also known as solvent naphtha, heavy aromatic, high flash aromatic naphtha type II, heavy aromatic solvent naphtha, hydrocarbons, C10-13 aromatics, >1% naphthalene, A200, and 5200 (Solvesso 200).

The aromatic solvents used in some embodiments, are naphthalene depleted ("ND"), or contain less than about 1% naphthalene. Said solvents can be added to the microcapsule suspension formulation prior to crystal formation as a preventative measure, or added to the microcapsule suspension formulation after crystal formation as a remedial measure to remove or reduce the presence of crystals.

The ester compounds used in some embodiments as hydrophobic crystal inhibitor additives include: 2,2,4-trimethyl-1,3-pentanediol monoisobutyrate.

Additionally, the microcapsule suspension formulations of the present disclosure can be combined or used in conjunction with pesticides, including arthropodicides, bactericides, fungicides, herbicides, insecticides, miticides, nematicides, nitrification inhibitors, such as dicyandiamide, urease inhibitors such as N-(n-butyl) thiophosphoric triamide, and the like or pesticidal mixtures and synergistic mixtures thereof. In such applications, the microcapsule suspension formulation of the present disclosure can be tank mixed with the desired pesticide(s) or they can be applied sequentially.

In a first embodiment, a microcapsule suspension formulation is disclosed comprising: (a) a suspended phase of a plurality of microcapsules having a volume median particle size of from about 1 to about 10 microns, wherein the microcapsules comprise: (1) a microcapsule wall produced by an interfacial polycondensation reaction between a polymeric isocyanate and a polyamine to form a polyurea shell; (2) at least one organic nitrification inhibiting compound encapsulated within the polyurea shell; (3) at least one polymeric ultra-hydrophobe compound encapsulated within the polyurea shell; and (b) an aqueous phase.

In a second embodiment, the aqueous phase of the microcapsule suspension formulation of the first embodiment further includes at least one additional ingredient selected from the group consisting of: hydrophobic crystal inhibitor additive, dispersant, nonionic polymer surfactant, antifoam, biocide, and mixtures thereof.

In a third embodiment, the microcapsules of any of the prior embodiments comprise 2-chloro-6-(trichloromethyl) pyridine.

In a fourth embodiment, the formulation of any of the prior embodiments further comprises an agricultural active ingredient selected from the group consisting of: arthropodicides, bactericides, fungicides, herbicides, insecticides, miticides, nematicides, fertilizers, dicyandiamide, urease inhibitors, and pesticidal mixtures and synergistic mixtures thereof.

In a fifth embodiment, the formulation of any of the prior embodiments comprises between about 25 weight percent and about 35 weight percent 2-chloro-6-(trichloromethyl) pyridine.

In a sixth embodiment, the formulation of any of the prior embodiments comprises between about 0.1 weight percent and about 2.00 weight percent of the at least one polymeric ultra-hydrophobe compound.

In a seventh embodiment, the microcapsules of any of the prior embodiments comprise a polybutene.

In an eighth embodiment, the aqueous phase of the microcapsule suspension formulation of any of the prior embodiments comprises between about 1.0 weight percent and about 4.0 weight percent of the hydrophobic crystal inhibitor additive.

In a ninth embodiment, the hydrophobic crystal inhibitor additive of any of the prior embodiments is at least one compound selected from the group consisting of: aromatic solvents such as, for example, naphthalene depleted heavy aromatics, and ester compounds such as, for example, 2,2, 4-trimethyl-1,3-pentanediol monoisobutyrate, and mixtures thereof.

In a tenth embodiment, the aqueous phase of the microcapsule suspension formulation of any of the prior embodiments comprises between about 1.0 weight percent and about 10 weight percent nonionic polymer surfactant.

In an eleventh embodiment, the nonionic polymer surfactant of any of the prior embodiments is a polyvinyl alcohol.

In a twelfth embodiment, the aqueous phase of the microcapsule suspension formulation of any of the prior embodiments includes at least one additive selected from the group consisting of: modified styrene acrylic polymeric surfactant, aqueous emulsion of polydimethylsiloxane concentrate, xanthan gum, microcrystalline cellulose, carboxymethyl-cellulose sodium, propylene glycol, a biocide and mixtures thereof.

In a thirteenth embodiment, the formulation of any of the prior embodiments comprises between about 40 weight percent and about 70 weight percent of the aqueous phase.

In a fourteenth embodiment, a method is disclosed for making a microcapsule suspension formulation comprising the steps of: (a) preparing a lipophilic phase comprising at least one lipophilic isocyanate and at least one polymeric ultra-hydrophobe by mixing said at least one lipophilic isocyanate and at least one polymeric ultra-hydrophobe with at least one molten, low melting-point organic nitrification inhibiting compound; (b) preparing an aqueous phase by dissolving and mixing in water at least one additive selected from the group consisting of: dispersants, nonionic polymer surfactants antifoams, biocides, and mixtures thereof; (c) combining the lipophilic phase and aqueous phase to form an oil-in-water emulsion; and (d) combining the oil-in-water emulsion with a solution of at least one polyamine in water to generate microcapsules.

In a fifteenth embodiment, the lipophilic phase of any of the prior embodiments comprises 2-chloro-6-(trichloromethyl)pyridine.

In a sixteenth embodiment, the lipophilic phase of any of the prior embodiments comprises between about 75 weight percent and about 90 weight percent 2-chloro-6-(trichloromethyl)pyridine.

In a seventeenth embodiment, the lipophilic phase of any of the prior embodiments comprises between about 0.1 weight percent and about 3.00 weight percent of the at least one polymeric ultra-hydrophobe compound.

In an eighteenth embodiment, the lipophilic phase of any of the prior embodiments comprises a polybutene.

In a nineteenth embodiment, the method of any of the prior embodiments further comprises the step of: adding at least one additive selected from the group consisting of: dispersants, antifoams, biocides, an aqueous emulsion of polydimethylsiloxane concentrate, a xanthan gum, a microcrystalline cellulose, a carboxymethyl-cellulose sodium, an anti-freeze additive selected from at least one of ethylene glycol, propylene glycol or glycerol, a hydrophobic crystal inhibitor additive and mixtures thereof, after the step of combining the oil-in-water emulsion with a solution of at least one polyamine in water to generate microcapsules. The method of any of the prior embodiments may also further comprise the step of adding at least one additive selected from the group consisting of: hydrophobic crystal inhibitor additive, dispersant, antifoam, biocide, and mixtures thereof after the step of combining the oil-in-water emulsion with a solution of at least one polyamine in water to generate microcapsules that form the aqueous microcapsule suspension.

In a twentieth embodiment, the final microcapsule suspension of any of the prior embodiments comprises between about 1.0 weight percent and about 4.0 weight percent of at least one hydrophobic crystal inhibitor additive.

In a twenty-first embodiment, the hydrophobic crystal inhibitor additive of any of the prior embodiments is at least one compound selected from the group consisting of: aromatic solvents, 2,2,4-trimethyl-1,3-pentanediol monoisobutyrate, and mixtures thereof.

In a twenty-second embodiment, the aqueous phase of any of the prior embodiments comprises between about 1.0 weight percent and about 10 weight percent of a nonionic polymer surfactant In a twenty-third embodiment, the nonionic polymer surfactant of any of the prior embodiments is a polyvinyl alcohol.

In a twenty-fourth embodiment, the final microcapsule suspension or the aqueous phase of any of the prior embodiments includes at least one additive selected from the group consisting of: a modified styrene acrylic polymeric surfactant, an aqueous emulsion of polydimethylsiloxane concentrate, a xanthan gum, a microcrystalline cellulose, a carboxymethyl-cellulose sodium, a propylene glycol, and mixtures thereof.

In a twenty-fifth embodiment, the aqueous phase of any of the prior embodiments includes at least one additive selected from the group consisting of: modified styrene acrylic polymeric surfactant, nonionic polymer, aqueous emulsion of polydimethylsiloxane concentrate, xanthan gum, microcrystalline cellulose, carboxymethyl-cellulose sodium, and mixtures thereof.

In a twenty-sixth embodiment, the formulation of any of the prior embodiments comprises between about 40 weight percent and about 70 weight percent of the aqueous phase.

In a twenty-seventh embodiment, the method of any of the prior embodiments further comprises the step of: controlling the temperature of the oil-in-water emulsion while mixing the lipophilic and aqueous phases to produce oily globules of a desired size.

In a twenty-eighth embodiment, the method of any of the prior embodiments further comprises the step of adding to the formulation an agricultural active ingredient selected from the group consisting of: pesticides, arthropodicides, bactericides, fungicides, herbicides, insecticides, miticides, nematicides, fertilizers, dicyandiamide, urease inhibitors, and pesticidal mixtures and synergistic mixtures thereof.

DETAILED DESCRIPTION (Trichloromethyl)pyridine compounds useful in the composition of the present disclosure include compounds having a pyridine ring which is substituted with at least one trichloromethyl group and mineral acid salts thereof. Suitable compounds include those containing chlorine or methyl substituents on the pyridine ring in addition to a trichloromethyl group, and are inclusive of chlorination products of methyl pyridines such as lutidine, collidine and picoline. Suitable salts include hydrochlorides, nitrates, sulfates and phosphates. The (trichloromethyl)pyridine compounds useful in the practice of the present disclosure are typically oily liquids or crystalline solids dissolved in a solvent. Other suitable compounds are described in U.S. Pat. No. 3,135,594. A preferred (trichloromethyl)pyridine is 2-chloro-6-(trichloromethyl)pyridine, also known as nitrapyrin, and the active ingredient of the product N-SERVE™. (Trademark of Dow AgroSciences LLC).

The utility of compounds such as nitrapyrin has been greatly increased by encapsulating such compounds along with suitable solvents in microcapsules. Especially useful microcapsules are comprised of a nitrapyrin/hydrophobic solvent core surround by a polyurea shell. Microcapsules of appropriate volume, shell thickness, and composition can be suspended in, stored in, and applied in an aqueous phase. Such useful formulations are disclosed in U.S. patent application Ser. No. 12/393,661 filed on Feb. 26, 2009, publication number U.S. 2009-0227458 A1 published on Sep. 10, 2009, and now issued as U.S. Pat. No. 8,741,805 issued on Jun. 3, 2014; U.S. Patent Application Ser. No. 12/009,432, filed Jan. 18, 2008, publication number U.S. 2008-0176745 A1 published on Jul. 24, 2008, and now issued as U.S. Pat. No. 8,377,849 issued on Feb. 19, 2013; and U.S. Provisional Application Ser. No. 60/881,680 filed on Jan. 22, 2007, which are all expressly incorporated by reference herein in their entirety as if each were incorporated by reference individually.

While the microcapsule aqueous suspensions referred to above are more stable than un-encapsulated nitrapyrin in an aqueous solution under certain conditions, it has been observed that crystals of nitrapyrin can form in the aqueous phase of a microcapsule suspension of nitrapyrin. Formation of crystalline nitrapyrin in an aqueous microcapsule suspension of nitrapyrin appears to be favored over a narrow temperature range of about −5° C. to about 15° C., more particularly about 0° C. to 10° C. (degrees centigrade).

The weight percentage of crystalline nitrapyrin in the bulk aqueous phase of the microcapsule suspension accumulates over time. Depending upon how the microcapsule suspensions are handled, the presence of measurable levels of crystalline nitrapyrin in the aqueous phase can be of little-to-no consequence or problematic. The presence of even about 0.1 wt. percent crystalline nitrapyrin or above in the aqueous phase of the microcapsule suspension can be especially problematic if the suspension is applied by spraying the suspension through a fine point nozzle with a sprayer containing inline screens.

Additionally, certain commercial embodiments of capsule suspensions of polyurea microencapsulated nitrification inhibitors, such as, for example, Instinct® or Entrench® (commercial products of Dow AgroSciences LLC), are limited by the amount of active ingredient (nitrification inhibitor) that can be microencapsulated and suspended in the aqueous phase without the active ingredient crystallizing into the aqueous phase. For example, in some embodiments, Instinct® and Entrench® comprise about 17% to about 18% by weight active ingredient (nitrapyrin). Crystallization of the active ingredient into the aqueous phase has limited the use of increased levels of active ingredient in the capsule suspensions. Some commercial nitrapyrin capsule suspension formulations have active loadings of 200 g/L, the upper limit of the loading being bound by the solubility of the nitrapyrin in a hydrophobic solvent. In some embodiments of the present disclosure, no oil/hydrophobic solvent is required to dissolve the nitrapyrin (and/or other active ingredient) in the lipophilic phase, and aqueous capsule suspensions formulations stable up to 300 g/L nitrapyrin are disclosed, without crystallization issues.

In some embodiments of the microcapsule suspension formulations of the present disclosure, stable, high-load, agricultural liquid formulations comprising aqueous microcapsule suspensions containing low melting active ingredients are presented. In some embodiments, the microcapsule suspension formulations are prepared without use of an organic solvent to dissolve the agricultural active, such as, for example, nitrification inhibitors such as nitrapyrin, by use of a polymeric ultra-hydrophobe which is added prior to microcapsule formation and ultimately ends up inside the microcapsule, a nonionic polymer, and a hydrophobic crystal inhibitor additive that is post added to the high-load microcapsule suspension. In some embodiments, the formulations provide superior physical, chemical, and crystallization stability upon storage, and acceptable volatility and nitrification inhibition attributes in applications to the soil.

Exemplary polymeric ultra-hydrophobes include polybutene, such as is commercially available as Indopol® Polybutene Grade: H-15 by INEOS Oligomers. Exemplary nonionic polymers include, but are not limited to, polyvinyl alcohols ("PVA").

Exemplary hydrophobic crystal inhibitor additives (optionally applied during manufacture and/or post-manufacture, "post-addition crystal inhibitor additives") include ester compounds such as 2,2,4-trimethyl-1,3-pentanediol monoisobutyrate, commercially available as UCAR® Filmer IBT (Dow Chemical; Midland, Mich.), and aromatic solvents such as: light aromatics, naphthalene depleted light aromatics, heavy aromatics, and/or naphthalene depleted heavy aromatics, such as, for example, Aromatic 200ND.

Exemplary hydrophobic crystal inhibitor additives comprise aromatic solvents and ester compounds. Hydrophobic crystal inhibitor additives of the present disclosure can be added to capsule suspensions of polyurea microencapsulated nitrapyrin in any weight percent range formed between any lower amount including from about 0.01 wt. %, 0.05 wt. %, 0.10 wt. %, 0.25 wt. %, 0.50 wt. %, 0.75 wt. %, and about 1.00 wt. % and any upper amount including about 10.00 wt. %, 7.50 wt. %, 5.00 wt. %, 3.00 wt. %, 2.50 wt. %, 2.00 wt. %, and about 1.50 wt. %.

In some embodiments, the aromatic solvents or ester compounds of the present disclosure can be added to aqueous capsule suspensions of polyurea microencapsulated nitrapyrin in any weight percent range selected from the group consisting of: between about 2.00 wt. % and about 3.00 wt. %, between about 1.00 wt. % and about 5.00 wt. %, between about 0.50 wt. % and about 7.50 wt. %, and between about 0.01 wt. % and about 10.00 wt. %.

A broad list of typical solvents and compounds which can be used to dissolve crystalline (trichloromethyl)pyridine compounds and thereby be used as hydrophobic crystal inhibitor additives include aromatic solvents, particularly alkyl substituted benzenes such as xylene or propylbenzene fractions, and mixed naphthalene and alkyl naphthalene fractions; mineral oils; kerosene; dialkyl amides of fatty acids, particularly the dimethylamides of fatty acids such as the dimethyl amide of caprylic acid; chlorinated aliphatic and aromatic hydrocarbons such as 1,1,1-trichloroethane and chlorobenzene; esters of glycol derivatives, such as the acetate of the n-butyl, ethyl, or methyl ether of diethyleneglycol and the acetate of the methyl ether of dipropylene glycol; ester compounds like 2,2,4-trimethyl-1,3-pentanediol monoisobutyrate, ketones such as isophorone and trimethylcyclohexanone (dihydroisophorone); and the acetate products such as hexyl or heptyl acetate. The preferred solvents and compounds which can be used to dissolve crystalline (trichloromethyl)pyridine compounds are xylene, alkyl substituted benzenes, such as propyl benzene fractions, alkyl naphthalene fractions and 2,2,4-trimethyl-1,3-pentanediol monoisobutyrate.

The microcapsules useful in the present disclosure can be prepared by the polycondensation reaction of a polymeric isocyanate and a polyamine to form a polyurea shell. Methods of microencapsulation are well known in the art and any such method can be utilized in the present disclosure to provide the capsule suspension formulation. In general, the capsule suspension formulation can be prepared by first mixing a polymeric isocyanate with a (trichloromethyl)pyridine, and/or other low-melting point agricultural active, and optionally, an ultra-hydrophobic compound such as a polymeric ultra-hydrophobe. This mixture is then combined with an aqueous phase, which optionally includes an emulsifier to form a two phase system. The organic phase is emulsified into the aqueous phase by shearing until the desired particle size is achieved. An aqueous crosslinking polyamine solution is then added dropwise while stirring to form the encapsulated particles of (trichloromethyl)pyridine in an aqueous suspension. Alternatively, an oil-in-water emulsion can be added to an aqueous solution of a polyamine under shearing to form the microcapsules. In some embodiments, the microcapsules of in the present disclosure can be prepared by a batch processing method, a continuous processing method, or a combination of a batch process and a continuous process.

The desired particle size and cell wall thickness will depend upon the actual application. The microcapsules typically have a volume median particle size of from about 1 to about 10 microns and a capsule wall thickness of from about 50 to about 125 nanometers. In another embodiment, requiring soil surface stability, the desired particle size may be from about 1-5 microns, with cell wall thicknesses of from about 75 to about 125 nanometers.

Other conventional additives may also be incorporated into the exemplary formulations such as, for example, emulsifiers, dispersants, thickeners, biocides, pesticides, salts and film-forming polymers.

Dispersing and emulsifying agents, known as surface-active agents or surfactants, include condensation products of alkylene oxides with phenols and organic acids, alkyl aryl sulfonates, modified styrene acrylic polymeric surfactants, polyoxyalkylene derivatives of sorbitan esters, complex ether alcohols, mahogany soaps, lignin sulfonates, polyvinyl alcohols, and the like. The surface-active agents are generally employed in the amount of from about 1 to about 20 percent by weight of the microcapsule suspension formulation.

The weight ratio of the suspended phase to the aqueous phase within the microcapsule suspension formulation of the present disclosure is dependent upon the desired concentration of (trichloromethyl)pyridine compound in the final formulation. Typically, the weight ratio will be from about 1:0.75 to about 1:20. Generally the desired ratio is about 1:1 to about 1:7, and is preferably from about 1:1 to about 1:4. The ratio may also be in the range of about 1:1 to about 1:2.

The presence of a (trichloromethyl)pyridine compound suppresses the nitrification of ammonium nitrogen in the soil or growth medium by inhibiting the activity of certain microbes present in the soil, thereby preventing the rapid loss of ammonium nitrogen from sources such as nitrogen fertilizers, organic nitrogen constituents, and/or organic fertilizers and the like.

Generally, the microcapsule suspension formulations of the present disclosure are applied such that the (trichloromethyl)pyridine compound is applied to the soil or a growth medium at a rate of from about 0.5 to about 1.5 kg/hectare, preferably at a rate of from about 0.58 to about 1.2 kg/hectare. The preferred amount can be ascertained by the application preference, considering factors such as soil pH, temperature, soil type and mode of application.

The microcapsule suspension formulations of the present disclosure can be applied in any manner which will benefit the crop of interest. In one embodiment, the microcapsule suspension formulation is applied to growth medium in a band or row application. In another embodiment, the formulation is applied to or throughout the growth medium prior to seeding or transplanting the desired crop plant. In yet another embodiment, the formulation can be applied to the root zone of growing plants.

Additionally, the microcapsule suspension formulation can be applied with the application of nitrogen fertilizers. The formulation can be applied prior to, subsequent to, or simultaneously with the application of fertilizers.

The microcapsule suspension formulations of the present disclosure have the added benefit that they are stable enough that they can be applied to the soil surface, without having to immediately add additional water or using mechanical incorporation in order to mix the formula into the soil; in some embodiments the formula can reside on the surface of the soil for days or even weeks. Alternatively, if desired, the formulations of the present disclosure can be incorporated into the soil directly upon application.

The microcapsule suspension formulations of the present disclosure typically have a concentration of (trichloromethyl)pyridine compound in amounts of from about 5, preferably from about 10 and more preferably from about 15 to about 40, typically to about 35, preferably to about 30 and more preferably to between about 25 percent by weight and 27 percent by weight, based on the total weight of the microcapsule suspension formulation. The microcapsule suspension formulations are then optionally mixed with one or more solvents and/or water to obtain the desired rate for application.

Soil treatment compositions may be prepared by dispersing the microcapsule suspension formulation in fertilizers such as ammonium or organic nitrogen fertilizer. The resulting fertilizer composition may be employed as such or may be modified, as by dilution with additional nitrogen fertilizer or with inert solid carrier to obtain a composition comprising any desired amount of active agent for treatment of soil.

The soil may be prepared in any fashion with the microcapsule suspension formulations of the present disclosure, including mechanically mixed with the soil; applied to the surface of the soil and thereafter dragged or diced into the soil to a desired depth; or by being directly transported into the soil by method such as by: injection, spraying, dusting or irrigation. In irrigation applications, the formulations may be introduced to irrigation water in an appropriate amount in order to obtain a distribution of the (trichloromethyl)pyridine compound to the desired depth of up to 6 inches (15.24 cm.).

Surprisingly, once incorporated into the soil, the microcapsule suspension formulations of the present disclosure outperform other nitrapyrin formulations, especially unencapsulated versions. It was thought that the encapsulated composition would not release nitrapyrin sufficiently to be as effective as the non-encapsulated versions, wherein the diffusion from the capsule would be too slow to provide a biological effect, but in fact, the opposite effect is observed.

The controlled release of nitrapyrin in the microcapsule suspension formulations of the present disclosure exhibits certain advantages over the application of encapsulated nitrapyrin. First, the amount of nitrapyrin can be reduced since it is more efficiently released into the soil over an extended period of time. Secondly, if desired, the microcapsule suspension formulations of the present disclosure can be applied and left on the surface to be naturally incorporated into the soil, without the need for mechanical incorporation.

In some embodiments, the hydrophobic crystal inhibitor additives are added to the aqueous phase of microcapsule suspension formulations that include nitrapyrin in order to reduce the rate of nitrapyrin crystal formation and/or growth in the aqueous phase at certain temperature and/or storage conditions. In some embodiments, hydrophobic crystal inhibitor additives added after the formation of nitrapyrin crystals has occurred, provide superior crystal growth reduction under temperature and/or storage conditions known to promote nitrapyrin crystal growth. In some exemplary embodiments, the hydrophobic crystal inhibitor additives include at least one oil and are present in the aqueous phase of the formulations after the formation of the microcapsules.

Some embodiments include microcapsule suspension formulations that already include crystals of nitrapyrin and that do not include hydrophobic crystal inhibitor additives in the aqueous phase. These suspensions can be treated with one or more hydrophobic crystal inhibitor additives by adding them to the aqueous phase of the suspension. The resulting mixture can be stirred at ambient temperature for a length of time, possibly 30 minutes to 5 hours based on the total volume of the microcapsule suspension, until the crystals of nitrapyrin, or similar crystalized organic nitrification inhibitor/agricultural active compound, have disappeared.

Formulations of the present disclosure include capsule suspension concentrates of microcapsules suspended in aqueous solution, wherein the microcapsules comprise at least one low-melting point agricultural active ingredient and at least one ultra-hydrophobic compound. The aqueous phase may optionally comprise at least one nonionic polymer, and, optionally, at least one or more additional hydrophobic crystal inhibitor additives post-added to the formulations to stabilize the crystal growth issues of active ingredients in the continuous aqueous phase. High-load nitrapyrin capsule suspensions (greater than about 200 g/L active ingredient) may form nitrapyrin crystals in the aqueous phase at mild cold storage temperatures, about 10° C. The nitrapyrin crystals may be about 99% pure. Under some conditions, over time, such crystals may compose up to 0.5 weight percent of the overall microcapsule suspension formulations. Crystals may form at temperatures including 0° C.-5° C., and 15° C. Solvent-based crystal growth inhibitors such as the hydrophobic crystal inhibitor additives can provide superior physical stability, particularly at mild cold storage temperatures at about 10° C., to prevent crystal formation in the aqueous phase of the microcapsule suspension.

Illustratively, post-added hydrophobic crystal inhibitor additives that are aromatic solvents include: Aromatic 100 Fluid, also known as solvent naphtha or light aromatic; Aromatic 150 Fluid, also known as solvent naphtha, heavy aromatic, high flash aromatic naphtha type II, heavy aromatic solvent naphtha, hydrocarbons, C10 aromatics, >1% naphthalene, A150, 5150 (Solvesso 150); and Aromatic 200 Fluid, also known as solvent naphtha, heavy aromatic, high flash aromatic naphtha type II, heavy aromatic solvent naphtha, hydrocarbons, C10-13 aromatics, >1% naphthalene, A200, and 5200 (Solvesso 200).

The aromatic solvents, in some embodiments, are naphthalene depleted ("ND"), or contain less than about 1% naphthalene. Said solvents can be added to the microcapsule suspension formulation prior to crystal formation as a preventative measure, or added to the microcapsule suspension formulation after crystal formation as a remedial measure to remove or reduce the presence of crystals.

The exemplary formulations of the present disclosure may further comprise any combination of stabilizers, thickeners, dispersants, biocides, surfactants, plasticizers, and/or solvents known to those of ordinary skill in the art to adapt the viscosity, flowability, density, thickness, and/or stability of the formulations.

Additionally, the microcapsule suspension formulations of the present disclosure can be combined or used in conjunction with pesticides, including arthropodicides, bactericides, fungicides, herbicides, insecticides, miticides, nematicides, nitrification inhibitors such as dicyandiamide, urease inhibitors such as N-(n-butyl) thiophosphoric triamide, and the like or pesticidal mixtures and synergistic mixtures thereof. In such applications, the microcapsule suspension formulation of the present disclosure can be tank mixed with the desired pesticide(s) or they can be applied sequentially.

Exemplary herbicides include, but are not limited to acetochlor, alachlor, aminopyralid, atrazine, benoxacor, bromoxynil, carfentrazone, chlorsulfuron, clodinafop, clopyralid, dicamba, diclofop-methyl, dimethenamid, fenoxaprop, flucarbazone, flufenacet, flumetsulam, flumiclorac, fluroxypyr, glufosinate-ammonium, glyphosate, halosulfuronmethyl, imazamethabenz, imazamox, imazapyr, imazaquin, imazethapyr, isoxaflutole, quinclorac, MCPA, MCP amine, MCP ester, mefenoxam, mesotrione, metolachlor, s-metolachlor, metribuzin, metsulfuron methyl, nicosulfuron, paraquat, pendimethalin, picloram, primisulfuron, propoxycarbazone, prosulfuron, pyraflufen ethyl, rimsulfuron, simazine, sulfosulfuron, thifensulfuron, topramezone, tralkoxydim, triallate, triasulfuron, tribenuron, triclopyr, trifluralin, 2,4-D, 2,4-D amine, 2,4-D ester and the like Exemplary insecticides include, but are not limited to 1,2 dichloropropane, 1,3 dichloropropene, abamectin, acephate, acequinocyl, acetamiprid, acethion, acetoprole, acrinathrin, acrylonitrile, alanycarb, aldicarb, aldoxycarb, aldrin, allethrin, allosamidin, allyxycarb, alpha cypermethrin, alpha ecdysone, amidithion, amidoflumet, aminocarb, amiton, amitraz, anabasine, arsenous oxide, athidathion, azadirachtin, azamethiphos, azinphos ethyl, azinphos methyl, azobenzene, azocyclotin, azothoate, barium hexafluorosilicate, barthrin, benclothiaz, bendiocarb, benfuracarb, benoxafos, bensultap, benzoximate, benzyl benzoate, beta cyfluthrin, beta cypermethrin, bifenazate, bifenthrin, binapacryl, bioallethrin, bioethanomethrin, biopermethrin, bistrifluron, borax, boric acid, bromfenvinfos, bromo DDT, bromocyclen, bromophos, bromophos ethyl, bromopropylate, bufencarb, buprofezin, butacarb, butathiofos, butocarboxim, butonate, butoxycarboxim, cadusafos, calcium arsenate, calcium polysulfide, camphechlor, carbanolate, carbaryl, carbofuran, carbon disulfide, carbon tetrachloride, carbophenothion, carbosulfan, cartap, chinomethionat, chlorantraniliprole, chlorbenside, chlorbicyclen, chlordane, chlordecone, chlordimeform, chlorethoxyfos, chlorfenapyr, chlorfenethol, chlorfenson, chlorfensulphide, chlorfenvinphos, chlorfluazuron, chlormephos, chlorobenzilate, chloroform, chloromebuform, chloromethiuron, chloropicrin, chloropropylate, chlorphoxim, chlorprazophos, chlorpyrifos, chlorpyrifos methyl, chlorthiophos, chromafenozide, cinerin I, cinerin II, cismethrin, cloethocarb, clofentezine, closantel, clothianidin, copper acetoarsenite, copper arsenate, copper naphthenate, copper oleate, coumaphos, coumithoate, crotamiton, crotoxyphos, cruentaren A &B, crufomate, cryolite, cyanofenphos, cyanophos, cyanthoate, cyclethrin, cycloprothrin, cyenopyrafen, cyflumetofen, cyfluthrin, cyhalothrin, cyhexatin, cypermethrin, cyphenothrin, cyromazine, cythioate, d-limonene, dazomet, DBCP, DCIP, DDT, decarbofuran, deltamethrin, demephion, demephion O, demephion S, demeton, demeton methyl, demeton O, demeton O methyl, demeton S, demeton S methyl, demeton S methylsulphon, diafenthiuron, dialifos, diamidafos, diazinon, dicapthon, dichlofenthion, dichlofluanid, dichlorvos, dicofol, dicresyl, dicrotophos, dicyclanil, dieldrin, dienochlor, diflovidazin, diflubenzuron, dilor, dimefluthrin, dimefox, dimetan, dimethoate, dimethrin, dimethylvinphos, dimetilan, dinex, dinobuton, dinocap, dinocap 4, dinocap 6, dinocton, dinopenton, dinoprop, dinosam, dinosulfon, dinotefuran, dinoterbon, diofenolan, dioxabenzofos, dioxacarb, dioxathion, diphenyl sulfone, disulfiram, disulfoton, dithicrofos, DNOC, dofenapyn, doramectin, ecdysterone, emamectin, EMPC, empenthrin, endosulfan, endothion, endrin, EPN, epofenonane, eprinomectin, esfenvalerate, etaphos, ethiofencarb, ethion, ethiprole, ethoate methyl, ethoprophos, ethyl DDD, ethyl formate, ethylene dibromide, ethylene dichloride, ethylene oxide, etofenprox, etoxazole, etrimfos, EXD, famphur, fenamiphos, fenazaflor, fenazaquin, fenbutatin oxide, fenchlorphos, fenethacarb, fenfluthrin, fenitrothion, fenobucarb, fenothiocarb, fenoxacrim, fenoxycarb, fenpirithrin, fenpropathrin, fenpyroximate, fenson, fensulfothion, fenthion, fenthion ethyl, fentrifanil, fenvalerate, fipronil, flonicamid, fluacrypyrim, fluazuron, flubendiamide, flubenzimine, flucofuron, flucycloxuron, flucythrinate, fluenetil, flufenerim, flufenoxuron, flufenprox, flumethrin, fluorbenside, fluvalinate, fonofos, formetanate, formothion, formparanate, fosmethilan, fospirate, fosthiazate, fosthietan, fosthietan, furathiocarb, furethrin, furfural, gamma cyhalothrin, gamma HCH, halfenprox, halofenozide, HCH, HEOD, heptachlor, heptenophos, heterophos, hexaflumuron, hexythiazox, HHDN, hydramethylnon, hydrogen cyanide, hydroprene, hyquincarb, imicyafos, imidacloprid, imiprothrin, indoxacarb, iodomethane, IPSP, isamidofos, isazofos, isobenzan, isocarbophos, isodrin, isofenphos, isoprocarb, isoprothiolane, isothioate, isoxathion, ivermectin jasmolin I, jasmolin II, jodfenphos, juvenile hormone I, juvenile hormone II, juvenile hormone III, kelevan, kinoprene, lambda cyhalothrin, lead arsenate, lepimectin, leptophos, lindane, lirimfos, lufenuron, lythidathion, malathion, malonoben, mazidox, mecarbam, mecarphon, menazon, mephosfolan, mercurous chloride, mesulfen, mesulfenfos, metaflumizone, metam, methacrifos, methamidophos, methidathion, methiocarb, methocrotophos, methomyl, methoprene, methoxychlor, methoxyfenozide, methyl bromide, methyl isothiocyanate, methylchloroform, methylene chloride, metofluthrin, metolcarb, metoxadiazone, mevinphos, mexacarbate, milbemectin, milbemycin oxime, mipafox, mirex, MNAF, monocrotophos, morphothion, moxidectin, naftalofos, naled, naphthalene, nicotine, nifluridide, nikkomycins, nitenpyram, nithiazine, nitrilacarb, novaluron, noviflumuron, omethoate, oxamyl, oxydemeton methyl, oxydeprofos, oxydisulfoton, paradichlorobenzene, parathion, parathion methyl, penfluron, pentachlorophenol, permethrin, phenkapton, phenothrin, phenthoate, phorate, phosalone, phosfolan, phosmet, phosnichlor, phosphamidon, phosphine, phosphocarb, phoxim, phoxim methyl, pirimetaphos, pirimicarb, pirimiphos ethyl, pirimiphos methyl, potassium arsenite, potassium thiocyanate, pp' DDT, prallethrin, precocene I, precocene II, precocene III, primidophos, proclonol, profenofos, profluthrin, promacyl, promecarb, propaphos, propargite, propetamphos, propoxur, prothidathion, prothiofos, prothoate, protrifenbute, pyraclofos, pyrafluprole, pyrazophos, pyresmethrin, pyrethrin I, pyrethrin II, pyridaben, pyridalyl, pyridaphenthion, pyrifluquinazon, pyrimidifen, pyrimitate, pyriprole, pyriproxyfen, quassia, quinalphos, quinalphos, quinalphos methyl, quinothion, quantifies, rafoxanide, resmethrin, rotenone, ryania, sabadilla, schradan, selamectin, silafluofen, sodium arsenite, sodium fluoride, sodium hexafluorosilicate, sodium thiocyanate, sophamide, spinetoram, spinosad, spirodiclofen, spiromesifen, spirotetramat, sulcofuron, sulfiram, sulfluramid, sulfotep, sulfur, sulfuryl fluoride, sulprofos, tau fluvalinate, tazimcarb, TDE, tebufenozide, tebufenpyrad, tebupirimfos, teflubenzuron, tefluthrin, temephos, TEPP, terallethrin, terbufos, tetrachloroethane, tetrachlorvinphos, tetradifon, tetramethrin, tetranactin, tetrasul, theta cypermethrin, thiacloprid, thiamethoxam, thicrofos, thiocarboxime, thiocyclam, thiodicarb, thiofanox, thiometon, thionazin, thioquinox, thiosultap, thuringiensin, tolfenpyrad, tralomethrin, transfluthrin, transpermethrin, triarathene, triazamate, triazophos, trichlorfon, trichlormetaphos 3, trichloronat, trifenofos, triflumuron, trimethacarb, triprene, vamidothion, vamidothion, vaniliprole, vaniliprole, XMC, xylylcarb, zeta cypermethrin and zolaprofos.

Additionally, any combination of one or more of the above pesticides can be used.

Additionally, Rynaxypyr™ (trademark of DuPont), an anthranilic diamide (Chlorantraniliprole) crop protection chemistry can be used to practice the invention.

As used throughout the specification, the term "about" refers to plus or minus 10% of the stated value, for example the term 'about 1.0' includes values from 0.9 to 1.1.

The following examples are provided to illustrate the present invention. The examples are not intended to limit the scope of the present invention and they should not be so interpreted. Amounts are in weight parts or weight percentages unless otherwise indicated.

EXAMPLES

High load nitrapyrin capsule suspension formulations were prepared by microencapsulation of oil-in-water emulsions. The major components of some exemplary formulations are shown in Table 1. The lipophilic oil phase of the oil-in-water emulsions was prepared by mixing polymethylene polyphenylisocyanate (PAPI 27) and polybutene (Indopol® Polybutene Grade: H-15 by INEOS Oligomers, one embodiment of a "polymeric ultra-hydrophobe") in molten nitrapyrin technical (melting point: ~63° C.) at 70° C. Nitrapyrin technical comprises about 90% to about 100% pure nitrapyrin depending on the impurity level (shown in Table 1 below).

One of skill in the chemical arts could select one or more other suitable isocyanates, polymeric ultra-hydrophobes, and/or agricultural active compounds, optionally nitrification inhibitor(s), for combination in the lipophilic oil phase. For example, any combination of isocyanate(s), polymeric ultra-hydrophobe(s), and low-melting point organic nitrification inhibitor(s) that exhibited good solubility when mixed together, and good stability once microencapsulated (as described below) would be suitable for use in the disclosed formulations. Moreover, other lipophilic agricultural active ingredients that exhibited good solubility when mixed together, and good stability once microencapsulated (as described below) would be suitable for use in the disclosed formulations, such as, for example, pesticides, fungicides, herbicides, miticides, arthropocides, bactericides, fertilizers, and mixtures thereof.

The aqueous phase of the oil-in-water emulsions was prepared by dissolving in water PVA (SELVOL 205); dispersant (modified styrene acrylic polymeric surfactant, Atlox Metasperse 500L); antifoam (30% aqueous emulsion of polydimethylsiloxane concentrate, Antifoam C); and a broad spectrum biocide such as a 20% aqueous dipropylene glycol solution of 1,2-benzisothiazolin-3-one for the preservation of product against spoilage from bacteria, yeasts, and/or fungi (Proxel GXL). Any combination of stabilizers, thickeners, dispersants, biocides, surfactants, plasticizers, and/or solvents known to those of ordinary skill in the art to adapt the viscosity, flowability, density, thickness, and/or stability of the formulations can be added to the aqueous phase.

The aqueous phase was held at 50° C. Next, the oil and aqueous phases were mixed together at 21 m/s tip speed in an IKA Magic Lab homogenizer. The generated oil-in-water emulsion (containing about 3 μm diameter globules) was then transferred to a well-mixed pot containing ethylenediamine ("EDA") solution in water to generate microcapsules with 100 nm capsule wall thickness. After 2 hours of mixing, the microcapsule formulations were further stabilized by adding Kelzan® S (industrial grade xanthan gum dispersible in aqueous solution), Avicel® CL-611 (microcrystalline cellulose and carboxymethylcellulose sodium), propylene glycol, and a hydrophobic crystal inhibitor additive (either UCAR® Filmer IBT or Aromatic 200ND).

Table 1 lists some exemplary compositions of stable, high-load nitrapyrin capsule suspension formulations, without an oil solvent within the microcapsules containing nitrapyrin, and with a post-added, hydrophobic crystal inhibitor additive.

TABLE 1

Example compositions of stable, high-load nitrapyrin CS formulations comprising post-added, hydrophobic crystal inhibitor additives.

| Ingredients | GF-3411 (Wt. %) | GF-3410 (Wt. %) | GF-3421 (Wt. %) | GF-3407 - Control (Wt. %) |
|---|---|---|---|---|
| Nitrapyrin (A.I.) | 25.97 | 26.71 | 25.97 | 26.71 |
| Impurity in technical solution | 2.89 | 2.64 | 2.89 | 2.64 |
| [1]Indopol ® H-15 | 0.71 | 0.36 | 0.71 | 0.36 |
| [2]PAPI 27 | 5.48 | 5.51 | 5.48 | 5.51 |
| Ethylenediamine (EDA) | 1.23 | 1.23 | 1.23 | 1.23 |
| [3]PVA (SELVOL 205) | 1.44 | 1.44 | 1.44 | 1.44 |
| [4]Atlox Metasperse 500L | 2.00 | 2.00 | 2.00 | 2.00 |
| [5]Antifoam C | 0.09 | 0.09 | 0.09 | 0.09 |
| [6]Proxel GXL | 0.1 | 0.1 | 0.1 | 0.1 |
| [7]UCAR Filmer IBT | 2.80 | 2.80 | — | — |
| [8]Aromatic 200ND* | — | — | 2.80 | — |
| [9]Kelzan S | 0.10 | 0.10 | 0.10 | 0.10 |
| [10]Avicel CL-611 | 0.20 | 0.20 | 0.20 | 0.20 |

TABLE 1-continued

Example compositions of stable, high-load nitrapyrin CS formulations comprising post-added, hydrophobic crystal inhibitor additives.

| Ingredients | GF-3411 (Wt. %) | GF-3410 (Wt. %) | GF-3421 (Wt. %) | GF-3407 - Control (Wt. %) |
|---|---|---|---|---|
| Propylene glycol | 10.00 | 10.00 | 10.00 | 10.00 |
| Water | 46.99 | 46.82 | 46.99 | 49.62 |

*GF-3421 resulted with 2 wt. % Aromatic 200ND instead of targeted 2.8 wt. %.
[1]Indopol ® H-15: Polybutene grade: H-15 by INEOS Oligomers.
[2]PAPI 27: Polymethylene Polyphenylisocyanate.
[3]PVA (SELVOL 205): polyvinyl alcohol, partially hydrolyzed.
[4]Atlox Metasperse 500L: dispersant, modified styrene acrylic polymeric surfactant.
[5]Antifoam C: 30% aqueous emulsion of polydimethylsiloxane concentrate.
[6]Proxel GXL: broad spectrum biocide for the preservation of industrial water-based products against spoilage from bacteria, yeasts, and fungi.
[7]UCAR ® Filmer IBT: 2,2,4-trimethyl-1,3-pentanediol monoisobutyrate.
[8]Aromatic 200ND: Naphthalene depleted heavy aromatic.
[9]Kelzan S: industrial grade xanthan gum dispersible in aqueous solution.
[10]Avicel CL-611: microcrystalline cellulose and carboxymethylcellulose sodium.

Some samples were tested for crystallization stability at different time intervals and at different temperatures and compared against the control sample, GF-3407, which had no crystal inhibitor additive. The results of these tests are summarized in Table 2.

Sill referring to Table 2, the wet sieve procedure determining the crystal content in the storage samples was carried out as follows: approximately 20 g of sample were added to a glass beaker containing between 100 and 200 grams of tap water. The solution was stirred using a glass stir rod and then poured through a 75 μm mesh sieve. The beaker was rinsed with additional water and the rinse was also poured through the sieve. Tap water was poured over the sample in the sieve for approximately 30 seconds to rinse weak agglomerates through. The residual left on the screen was rinsed onto a tared filter paper and vacuum filtered. This filter paper with sample was allowed to dry in a vacuum hood for at least four hours and then reweighed. Residue percentages were calculated using equation (1):

$$\text{Residue Percentage} = (\text{Filter paper and Residue Weight After Drying(g)} - \text{Filter Paper Weight (g)})/(\text{Total Sample Sieved(g)}) \quad (1)$$

This process was repeated for each storage stability sample and residue weight percentages were recorded as listed in the Table 2. Samples with UCAR® Filmer IBT and Aromatic 200ND showed less wet sieve residue wt. % values compared to control GF-3407 formulation in all storage conditions.

TABLE 2

Summary of testing the crystallization stability of some exemplary stable, high-load capsule suspensions compared to control sample GF-3407 without any hydrophobic crystal inhibitor additive

| | Wet Sieve (wt. %) | | | | | Storage |
|---|---|---|---|---|---|---|
| | Initial | FT[1] | 10° C. | 40° C. | 54° C. | Time |
| Control GF-3407 | — | 0.8 | 0.41 | 0.85 | 1.53 | 2 Wks |
| GF-3411 | 0.03 | 0.02 | 0.01 | 0.02 | 0.10 | 2 Wks |
| | | 0.09 | 0.09 | 0.10 | 0.23 | 4 Wks |
| | | 0.09 | | 0.09 | 0.48 | 8 Wks |
| GF-3421[2] | — | 0.03 | 0.02 | 0.02 | 0.03 | 2 Wks |
| | | 0.16 | 0.14 | 0.14 | 0.20 | 4 Wks |
| | | 0.32 | — | 1.54 | 0.5 | 8 Wks |

[1]temperature cycles from −10 to 40° C.;
[2]GF-3421 contains 2 wt. % Aromatic 200ND instead of targeted 2.8 wt. %.

A nitrapyrin volatility study was carried out. Briefly, formulations, some of which included nitrapyrin, were diluted into water to a concentration of 20 µg/mL nitrapyrin. For each formulation, multiple jars containing 20 ppm nitrapyrin in 2 g of white quartz sand were prepared. Half of the prepared jars were kept closed while the other half were left open at ambient temperature. At periodic intervals, three replicate jars stored open and those stored closed were analyzed for residual nitrapyrin.

At each time point, nitrapyrin was extracted using an internal standard solution containing 20 µg/mL dibutyl phthalate and filtered into HPLC vials using syringe filters. The solutions were analyzed by HPLC using a Kinetix C18 (150 mm×4.6 mm×2.6 µm) column and a UV detector set at 270 nm.

Shown below in Table 3 are the results obtained by measuring assays for nitrapyrin following the application of a diluted N-Serve® formulation to sand. N-Serve® is an unencapsulated liquid formulation of nitrapyrin at about 22% active, commercially available from Dow AgroSciences LLC. The results show the percent nitrapyrin remaining in the open and closed containers tested at each time point.

TABLE 3

Results obtained for nitrapyrin following the application of a diluted N-Serve formulation to sand.

| | | % nitrapyrin remaining with respect to amount added | | | | | |
|---|---|---|---|---|---|---|---|
| Sample ID | Initial | Day 2 Open | Day 2 Closed | Day 4 Open | Day 4 Closed | Day 8 Open | Day 8 Closed |
| N-serve* | 113 | 0 | 15.9 | 0 | 13 | 0 | 9.2 |

*Commercially available liquid nitrogen stabilizer formulation comprising about 22% nitrapyrin.

Referring now to Table 4, results from assay for nitrapyrin levels in sand following the application of diluted GF-3421 and GF-3411 to the sand. The results show the percent nitrapyrin remaining in the open and closed containers tested at each time point.

TABLE 4

Results obtained by measuring the percent of nitrapyrin remaining in sand following the application of diluted GF-3421 and GF-3411 formulations to sand.

| | | % nitrapyrin remaining with respect to amount added* | | | | | |
|---|---|---|---|---|---|---|---|
| Sample ID | Initial | Day 5 Open | Day 5 Closed | Day 12 Open | Day 12 Closed | Day 19 Open | Day 19 Closed |
| GF-3421 | 92.6 | 76.5 | 76.9 | 68.5 | 71.4 | 72.3 | 74.7 |
| GF-3411 | 98.4 | 83.7 | 87.5 | 68.1 | 82.8 | 69.5 | 85.1 |

*The results shown in the table above is the average of analysis performed in triplicate.

Briefly, in a soil nitrification study, active soil samples (100 g) were spiked with ~250 mg ammonium sulfate, to provide a source of $NH_4^+$, and ~50 µg of nitrapyrin, applied as a diluted solution of the formulation in ammonium sulfate solution. At each time-point, a 10 g aliquot of soil was transferred into a 60-mL glass jar and ammonium was extracted using 2M potassium chloride solution. The ammonium present in solution was estimated colorimetrically using the "Phenol-Hypochlorite reaction for determination of ammonia" (M. W. Weatherburn, Analytical Chemistry, Vol 39, No. 8, July 1967).

Active soil containing a similar amount of ammonium sulfate but no nitrapyrin was used as the control. Referring now to Table 5, the amount of ammonium remaining at each time-point calculated based on the theoretical amount of ammonium added.

TABLE 5

Amount of ammonium remaining at each time-point calculated based on the theoretical amount of ammonium added.

| | % Ammonium remaining in soil with respect to initial amount | | | |
|---|---|---|---|---|
| Row Labels | Day 0 | Day 2 | Day 7 | Day 14 |
| NH4 Blank | 87 | 85 | 74 | 41 |
| GF-3410 | 89 | 90 | 93 | 47 |
| GF-3411 | 89 | 92 | 92 | 43 |
| GF-3421 | 87 | 89 | 92 | 46 |

While the novel technology has been illustrated and described in detail in the figures and foregoing description, the same is to be considered as illustrative and not restrictive in character, it being understood that only the preferred embodiments have been shown and described and that all changes and modifications that come within the spirit of the novel technology are desired to be protected. As well, while the novel technology was illustrated using specific examples, theoretical arguments, accounts, and illustrations, these illustrations and the accompanying discussion should by no means be interpreted as limiting the technology. All patents, patent applications, and references to texts, scientific treatises, publications, and the like referenced in this application are incorporated herein by reference in their entirety.

The invention claimed is:
1. A microcapsule suspension formulation comprising:
(a) a suspended phase of a plurality of microcapsules having a volume median particle size of from about 1 to about 10 microns, wherein the microcapsules comprise:
(1) a microcapsule wall produced by an interfacial polycondensation reaction between a polymeric isocyanate and a polyamine to form a polyurea shell;
(2) at least one organic nitrification inhibiting compound encapsulated within the polyurea shell;

(3) at least one polymeric ultra-hydrophobe compound encapsulated within the polyurea shell; and
(b) an aqueous phase including a hydrophobic crystal inhibitor additive.

2. The microcapsule suspension formulation according to claim 1, wherein the aqueous phase further includes at least one additional ingredient selected from the group consisting of: a dispersant, a nonionic polymer, an antifoam, and a biocide.

3. The microcapsule suspension formulation according to claim 1, wherein the microcapsules comprise 2-chloro-6-(trichloromethyl)pyridine.

4. The microcapsule suspension formulation according to claim 1, wherein the formulation further comprises an agricultural active ingredient selected from the group consisting of: arthropodicides, bactericides, fungicides, herbicides, insecticides, miticides, nematicides, fertilizers, dicyandiamide, urease inhibitors, and pesticidal mixtures thereof.

5. The microcapsule suspension formulation according to claim 3, wherein the formulation comprises between about 25 weight percent and about 35 weight percent 2-chloro-6-(trichloromethyl)pyridine.

6. The microcapsule suspension formulation according to claim 1, wherein the formulation comprises between about 0.1 weight percent and about 2.00 weight percent of the at least one polymeric ultra-hydrophobe compound.

7. The microcapsule suspension formulation according to claim 6, wherein the microcapsules comprise a polybutene.

8. The microcapsule suspension formulation according to claim 1, wherein the aqueous phase comprises between about 1.0 weight percent and about 4.0 weight percent of the hydrophobic crystal inhibitor additive.

9. The microcapsule suspension formulation according to claim 1, wherein the hydrophobic crystal inhibitor additive includes at least one compound selected from the group consisting of: aromatic solvents and 2,2,4-trimethyl-1,3-pentanediol monoisobutyrate.

10. The microcapsule suspension formulation according to claim 2, wherein the aqueous phase comprises between about 1.0 weight percent and about 10 weight percent nonionic polymer.

11. The microcapsule suspension formulation according to claim 10, wherein the nonionic polymer is a polyvinyl alcohol.

12. The microcapsule suspension formulation according to claim 1, wherein the aqueous phase includes at least one additive selected from the group consisting of: modified styrene acrylic polymeric surfactant, nonionic polymer, aqueous emulsion of polydimethylsiloxane concentrate, xanthan gum, microcrystalline cellulose, carboxymethyl-cellulose sodium, and propylene glycol.

13. The microcapsule suspension formulation according to claim 1, wherein the formulation comprises between about 40 weight percent and about 70 weight percent of the aqueous phase.

14. A method for making a microcapsule suspension formulation comprising the steps of:
(a) preparing a lipophilic phase comprising at least one lipophilic isocyanate and at least one polymeric ultra-hydrophobe by mixing said at least one lipophilic isocyanate and said at least one polymeric ultra-hydrophobe in at least one molten organic nitrification inhibiting compound;
(b) preparing an aqueous phase by dissolving and mixing in water at least one first additive selected from the group consisting of: a dispersant, a nonionic polymer, an antifoam, and a biocide;
(c) combining the lipophilic phase and aqueous phase to form an oil-in-water emulsion;
(d) combining the oil-in-water emulsion with a solution of at least one polyamine in water to generate microcapsules; and
(e) adding a hydrophobic crystal inhibitor additive after the step of combining the oil-in-water emulsion with the solution of at least one polyamine in water to form the microcapsule suspension formulation.

15. The method according to claim 14, wherein the lipophilic phase comprises 2-chloro-6-(trichloromethyl)pyridine.

16. The method according to claim 14, wherein the lipophilic phase comprises between about 75 weight percent and about 90 weight percent 2-chloro-6-(trichloromethyl)pyridine.

17. The method according to claim 14, wherein the lipophilic phase comprises between about 0.1 weight percent and about 3.00 weight percent of the at least one polymeric ultra-hydrophobe compound.

18. The method according to claim 17, wherein the lipophilic phase comprises a polybutene.

19. The method according to claim 17, further comprising the step of:
adding at least one second additive selected from the group consisting of: a dispersant, an antifoam, and a biocide after the step of combining the oil-in-water emulsion with the solution of at least one polyamine in water to form the microcapsule suspension.

20. The method according to claim 14, wherein the aqueous phase comprises between about 1.0 weight percent and about 4.0 weight percent of a hydrophobic crystal inhibitor additive.

21. The method according to claim 20, wherein the hydrophobic crystal inhibitor additive is at least one compound selected from the group consisting of: aromatic solvents and 2,2,4-trimethyl-1,3-pentanediol monoisobutyrate.

22. The method according to claim 14, wherein the aqueous phase comprises between about 1.0 weight percent and about 10 weight percent nonionic polymer.

23. The method according to claim 22, wherein the nonionic polymer is a polyvinyl alcohol.

24. The method according to claim 14, wherein the aqueous phase includes at least one additive selected from the group consisting of: a modified styrene acrylic polymeric surfactant, a nonionic polymer, an aqueous emulsion of polydimethylsiloxane concentrate, xanthan gum, microcrystalline cellulose, carboxymethyl-cellulose sodium, and propylene glycol.

25. The method according to claim 14, wherein the aqueous phase includes at least one additive selected from the group consisting of: a modified styrene acrylic polymeric surfactant, a nonionic polymer, an aqueous emulsion of polydimethylsiloxane concentrate, xanthan gum, microcrystalline cellulose, and carboxymethyl-cellulose sodium.

26. The method according to claim 14, wherein the formulation comprises between about 40 weight percent and about 70 weight percent of the aqueous phase.

27. The method according to claim 14, further comprising the step of: controlling the temperature of the oil-in-water emulsion while mixing the lipophilic phase with the aqueous phase to produce oily globules.

28. The method according to claim 14, wherein the method further comprises the step of adding to the formulation an agricultural active ingredient selected from the group consisting of: pesticides, arthropodicides, bactericides, fungicides, herbicides, insecticides, miticides, nematicides, fertilizers, dicyandiamide, urease inhibitors, and pesticidal mixtures thereof.

* * * * *